United States Patent [19]
Takezawa et al.

[11] Patent Number: 5,736,399
[45] Date of Patent: Apr. 7, 1998

[54] MEDIUM-PENETRATING CELL CULTURE CARRIER, A CULTURING METHOD AND A DEVICE USING THIS CARRIER

[75] Inventors: Toshiaki Takezawa; Katsutoshi Yoshizato, both of Hiroshima, Japan

[73] Assignee: Research Development Corporation of Japan, Saitama, Japan

[21] Appl. No.: 401,255

[22] Filed: Mar. 9, 1995

[30] Foreign Application Priority Data

Mar. 9, 1994 [JP] Japan .................................. 6-038878
Dec. 29, 1994 [JP] Japan .................................. 6-339979

[51] Int. Cl.$^6$ .............................. C12M 3/00; C12N 5/00
[52] U.S. Cl. ..................... 435/399; 435/402; 435/286.5; 435/299.1; 435/299.2
[58] Field of Search ..................... 435/240.23, 240.243, 435/176–182, 289.1, 286.5, 299.1, 299.2, 1.1, 399, 402

[56] References Cited

U.S. PATENT DOCUMENTS 4,963,489 10/1990 Naughton et al. ............. 435/1.1
5,478,739 12/1995 Slivka et al. ................. 435/240.23

FOREIGN PATENT DOCUMENTS 2178447 2/1987 United Kingdom .

OTHER PUBLICATIONS

Fleischmajer et al. Journal of Investigative Derm. vol. 97 (1991), pp. 638–643).

Primary Examiner—William H. Beisner
Attorney, Agent, or Firm—Wenderoth, Lind & Ponack

[57] ABSTRACT

The present invention provides a medium-penetrating culture carrier comprising a plurality of natural or synthetic threads or the woven body thereof, a method for adhering cells onto this carrier to allow them to be proliferated, and a device which is physically connected to the carrier for feeding a medium using this medium-penetrating culture carrier, which are able to culture three-dimensionally animal cells in order that they can effect self-assembly as they do in the living tissue or organ from which they are derived.

17 Claims, 27 Drawing Sheets

$\ell_1 = 2.5$ cm
$\ell_2 = 3.5$ cm
W = 2.0 cm
h = 1.0 cm

MEDIUM-PENETRATING CELL CULTURE CARRIER, A CULTURING METHOD AND A DEVICE USING THIS CARRIER

BACKGROUND OF THE INVENTION

1. Field of the Invention

The present invention relates to a medium-penetrating cell culture carrier, a method for culturing animal cells and a device using this method. More specifically, it relates to a culture carrier for culturing three dimensionally anchorage-dependent cells thereon, and a method for culturing the cells in a state closer to the state where they are in a living organism, a device therefor, and a very useful culture means as a specific organ model of an animal. The culture means is useful, for instance, in the development of hybrid-type artificial organs and in the evaluation of the effects and toxicity of new medicines as a alternative for animal experiments.

2. Description of Related Art

Conventionally, to develop various medical technologies and medicine, a diversity of animal experiments and cell culturing experiments have been performed.

However, experiments using animals and cultured cells are not complete as model experiments of the whole body or various organs of the human being, each having its own problems. The animal experiments possess, for example, advantages in their ability to analyze systemic response to the intended effect. On the other hand, the species differences between humans and animals have not always made the results obtained satisfactorily reliable. It has been also pointed out that numerous animals have to be sacrificed. The cell culture experiments, on the other hand, have advantages in that we can directly investigate the effect under consideration by culturing human cells, even the ones of the patient. Yet, ordinary cell culture is conducted in a two-dimensional plane, and hence the results obtained are greatly different from those in actual organs in which many cells are aggregated three dimensionally, in respect not only to histological differences, but also in the way cell functions are expressed.

For these reasons, attempts have been made to culture three-dimensionally the cells derived from animal tissues, including human ones, and to use the cultured cells to allow them to regenerate a structure like organs of the organism. Known as the three-dimensional culture method designed for that purpose are a method for embedding cells in collagen gels and culturing them three dimensionally, and a multicellular spheroid forming method, as developed by the inventor of the present invention, in which a culture substratum containing a temperature-sensitive polymer is used.

However, by the conventional three-dimensional cell culture method, the collagen gel culture method and the spheroid forming method have the following shortcomings. As the three-dimensional structural body of culture cells grows larger, it becomes difficult to supply nutrients to the interior cells. Simultaneously, it becomes impossible for the cells to discharge metabolites which they secrete (useful physiologically-active substances and harmful substances). Accordingly, in the three-dimensional structural body of cells developed by the conventional methods, the cells necrose with a longer culture time.

As a means to solve these problems, the inventor of the present invention has already proposed a culture carrier essentially comprising a plant-derived fibrous branch body and a method for using this to culture animal cells. More specifically, this carrier makes use of the fibrous roots isolated from plant seeds which have been subjected to a germination culture. Use of this carrier permits three-dimensional culture of cells in a state closer to the state where they are in a living organism.

However, the development had been hoped for culture carriers which it is easier to produce and handle and which offer superior performance as three-dimensional culture carrier. Studies and investigations on culture methods using a new culture carrier have been continuously undertaken by the inventor of this invention.

SUMMARY OF THE INVENTION

The present invention has been made considering these circumstances, and has the objective of overcoming the problems of the conventional method and the culture substratum used therefore, and of providing a novel culture carrier in which animal cells can proliferate three-dimensionally and show self-assembly at a high survival rate, and a new method for culturing cells and a device therefore utilizing it.

The instant invention provides a medium-penetrating cell culture carrier comprising a plurality of natural or synthetic threads or the woven body thereof.

The present invention also provides a cell culture means whereby this carrier is inserted into a culture vessel and cause a medium to penetrate the carrier for cell culture; and a cell culture device which has this carrier, a culture vessel into which it is to be inserted and a means for feeding a medium and in which the carrier is connected to this medium feeding means.

DETAILED DESCRIPTION OF THE INVENTION

Figure 1:
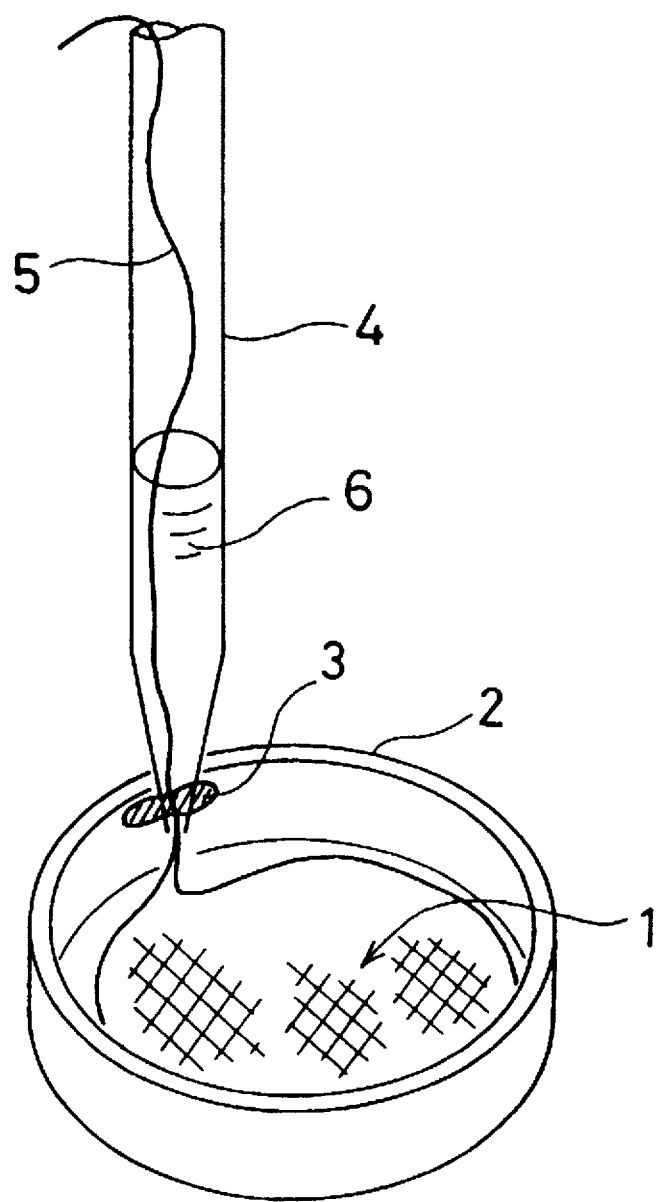
FIG. 1 shows a perspective diagram depicting an example of the culture device according to the present invention.

A cell culture carrier according to the present invention is composed of, for instance, a plurality of cotton, silk and other natural threads, or of nylon, acryl, polyester and other synthetic threads or the woven body thereof. The woven body in this case may be either a mesh or a gauze.

The threads having a diameter of scores to hundreds of µm in diameter or other types of threads can be combined for use. A plural kinds of threads or the woven body thereof, of, or those of the same kind but different in thread diameter, size of the opening mesh of the woven body and other physical shape and property may be employed.

Any of these must be so designed that an appropriate space geometry can be formed for the three-dimensional culture of cells. For the mesh body, this geometry has already been formed. A plurality of mesh bodies may be employed. For example, the mesh bodies with a mesh opening of 10 to 1000 µm, particularly of 200 to 400 µm, may be adequate for use in this application.

Water absorption required for the penetration of a media is greater for natural threads and the woven bodies thereof. Silk in particular absorbs about 1.5 times as much water as cotton. When these properties of thread materials, in addition to the cells to be handled and the culture conditions therefore, are considered, it is possible to construct the right carrier for the intended use.

It is also effective to provide this culture carrier made up of mesh and other woven bodies according to the present invention with the capability of being biodegradable in a living organism. This property makes it possible to culture cells in a living organism, and allow a culture carrier to be biodegraded by th organism and eliminated. This will make this sort of culture carrier very useful for medical applications.

This culture carrier offers the following advantages. Ascorbic acid is added to a culture medium to accelerate the proliferation of cells in a multilayer (three-dimensional) form. Or it is also possible to use a direct carrier of cells by providing the carrier with the capability of adhering cells thereon. In this case, extract matrix, gelatin, lectin, Mytilidae-derived adhesive proteins, polylysin, adhesive oligopeptide and/or thrombospongin provide means for making the carrier capable of adhering cells thereon. As the extracellular matrix, collage, fibronectin, hydronectin, laminin, proteoglycan, glycosaminoglycan are arbitrarily used.

Using these carriers, it is also effective to allow cells to be adhered locally at portions on a medium-penetrating cell culture carrier which are made capable of adhering them.

Furthermore, according to the present invention, when two or more kinds of cells are seeded simultaneously on a medium-penetrating cell culture carrier, it becomes possible to allow each cell species to adhere itself selectively to a portion provided with having the right cell-adhering capability.

This carrier can also be employed as an indirect carrier of cells, namely, as an extracellular matrix carrier. In this case, it is possible to embed cells into gels containing an extracellular matrix, such as collagen, gel and matrigel™.

The culture method according to the present invention makes it possible to seed anchorage-dependent animal cells suspended in a culture medium in a culture vessel in which said culture carrier is fixed, thereby causing the cell to adhere, spread, and proliferate in a multilayer (three-dimensional) form.

For animal cells, any specimen can be used that is collected from the body tissue or organ of every species including human. These cells may be the primary ones directly collected from a tissue or an organ, or may be the one obtained after generations of passage thereof. Moreover, animal cells may be mesencymal and/or epithelial normal cells, or may be mesencymal and/or epithelial cancer cells or other disease tissue cells.

Take, as an example, homo and hetero cell culture. It is illustrated to culture mesencymal cells and/or skin, liver, cancer and other epithelial cells. These are not the only cells that can be cultured by this method according to the present invention.

The cells adhered on a culture carrier spread, migrate and divide themselves therealong while proliferating in a multilayer (three-dimensional) form.

By the culture method according to the present invention, a culture medium is fed via said medium-penetrating cell culture carrier onto the carrier and the culture cells therearound. Even when th number of cells increase with extended terms of culture, this has inhibited some inner cells from necrosing. It is also possible to collect cell metabolites (useful physiologically-active agents and/or harmful wastes) with time not only from these inner cells, but also from the whole cell.

From the above, it is safe to state that this carrier can perform similar functions as capillaries do in a living tissue.

Comprising a culture carrier and an aggregate of culture cells, the multicellular aggregate can serve as a superb model of a living organ both in histological seractuves and in the expression of functions. Together with this, this aggregate could be applied to the development of artificial organs, the evaluation of the effect or toxicity of new medicine, and has added advantage that metabolites can be collected and measure with time in the selection of anticarcinogen and the evaluation of the metastasis capability of cancers.

This multicellular aggregate comprising a culture carrier (particularly, silk mesh) and an aggregate of culture cells can be considered to be applicable as the graft for treatment of vulnuses, including ambustion and decubitus. In this case, with its proven records as suture non-biodegradable in a living organism, silk insures its safety when used in an organism.

There is no specific limitation to the structure of a culture device, as long as said medium-penetrating cell culture carrier according to the present invention is utilized. Yet, as the means for feeding a culture medium, a pipette-like or a dropping pipette-like means may be employed which are vertically supported by a supporting stand or which, without use of any supporting means, is mounted on a culture vessel. Alternatively, the means may be equipped with a periscaltic pump.

Figure 2:
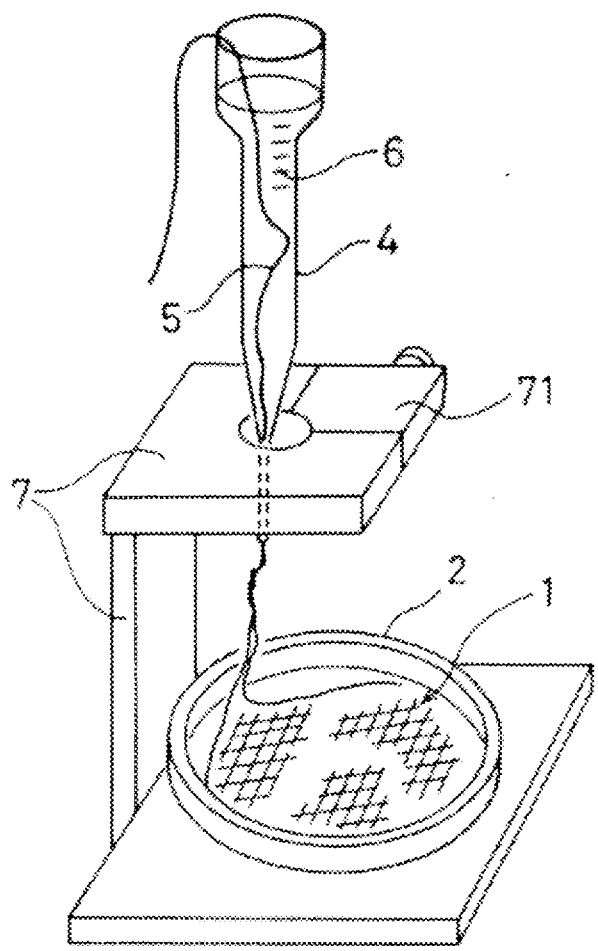
FIG. 2 shows a perspective diagram depicting another example of the culture device according to the present invention.

A simpler laboratory device is shown in, for instance, FIG. 1 and FIG. 2.

As illustrated in FIG. 1, a medium-penetrating carrier (1), a mesh body, according to the present invention is inserted into a culture vessel (2), said vessel (2) being adhered with a pipette means for feeding a culture medium (4) using an adhesive (3). The medium-penetrating carrier (1) is so constructed that one end thereof is inserted into the open end of this means for feeding a culture medium (4), that a thread portion extending upward (5) pulls up or relaxes the means, creating a restriction effect of the carrier at the opening end to control the amount of medium. A culture medium (6) is fed from the means for feeding the medium to the carrier.

As in FIG. 2, means for feeding a medium (4) are supplied by a support (7). These means are made removable by taking away a division part thereof (71).

The devices according to the present invention are not restricted to this simplified device.

Now, using example, a more detailed and specific descriptions will be given to this invention, but this invention is not limited to the following examples.

EXAMPLES

Example 1

(Production of a three-dimensional medium-penetrating device for culturing animal cells)

A piece of the sterilized gauze type III (K-pine; made by Kawamoto Bandaging Materials Ltd.) listed in Japan Pharmacopoeia was aseptically cut in a size about 2.0×10.0 cm, one side of the longitudinal ends of which is turned up about 1.0 cm; subsequently, on the central part of the turned up portion of the gauze approximately 30 cm-long sterilized silk surgical suture No. 4 (made by Murase Suture Manufacturing Co., Ltd.) was bound aseptically. Then, said suture was inserted through the suction end of a sterilized polypropylene pipette (Falcon #7575) which was cut into a tube at its clasping end aseptically, and pulled up into the clasping end thereof. This caused said gauze to be inserted and fixed partially at a thin tubular portion on the suction side. FIG. 2 shows the configuration of the preparation. In this figure, on the supporting stand made of an acryl plate which was sterilized by a 70% ethanol solution, the tubular part of the pipette was perpendicularly fixed so as to locate the suture upside and the gauze downside; thereafter, when approximately 5 ml of cell culture medium* (Dulbecco's modified Eagle's medium containing 10% fetal bovine serum, 20 mM HEPES, 100 units/ml penicillin and 100 μg/ml streptomycin) was filled, the culture medium was first absorbed by the cotton threads composing the gauze, distributed all over the gauze body, slowly dripping through the gauze and finally dropped down completely in several hours by dint of the gravity. Incidentally, the quantity of the medium fed per hour is adjustable by changing the strength of insertion of the gauze into the absorbing part (it was confirmed at 0.5 to 5.0 mg/hour).

As shown below in an example of specific applications of animal cell culturing method, the device is designed to culture animal cells in a three-dimensional state around the medium-penetrating gauze.

Example 2

(Method for three-dimensional culturing of animal cells on a medium-penetrating gauze)

The pipette having its clasping end cut off, in which the gauze attached with suture is inserted in the tubular part and fixed as shown in Example 1, was mounted vertically on the inside wall of hydrophobic polystyrene Petri dish (laboratory dish: φ35 mm Falcon #1008) with silicon adhesive. With the excessive amount of gauze cut off the bottom surface of the Petri dish, the whole dish was sterilized with ultraviolet ray. The gauze portion on the bottom surface of the Petri dish (a size of approximately 2.0×2.0 cm) was coated with about 0.3 ml of 0.5% type-I collagen solution (CELLGEN I-PC.Made by KOKEN Co.), and allowed to dry in the air aseptically, thereby making the gauze portion extend to become adhered tightly on the bottom surface of the Petri dish, and at the same time, providing it with cell adhering capability.

Figure 3:
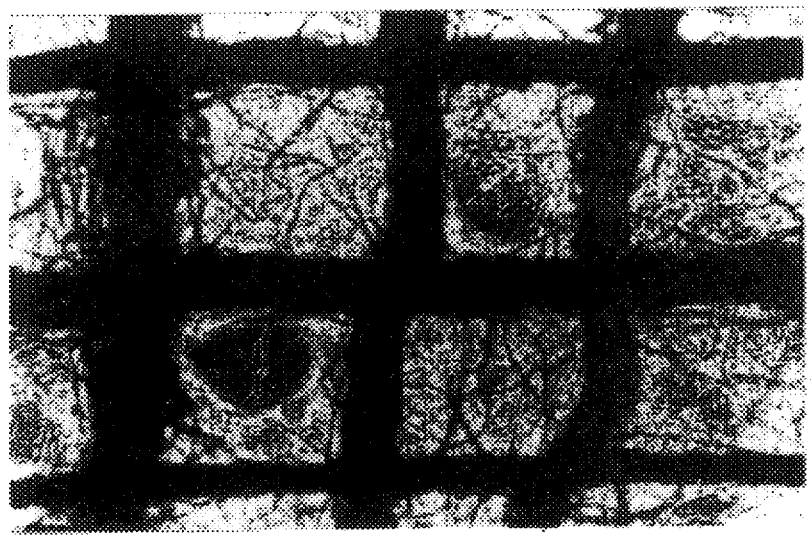
FIG. 3 shows a phase-contrast microphotograph and showing the 8th-day state of cells cultured by the method according to the present invention. 6.5 mm on the photograph is equivalent to 200 μm in an actual state.
Figure 4:
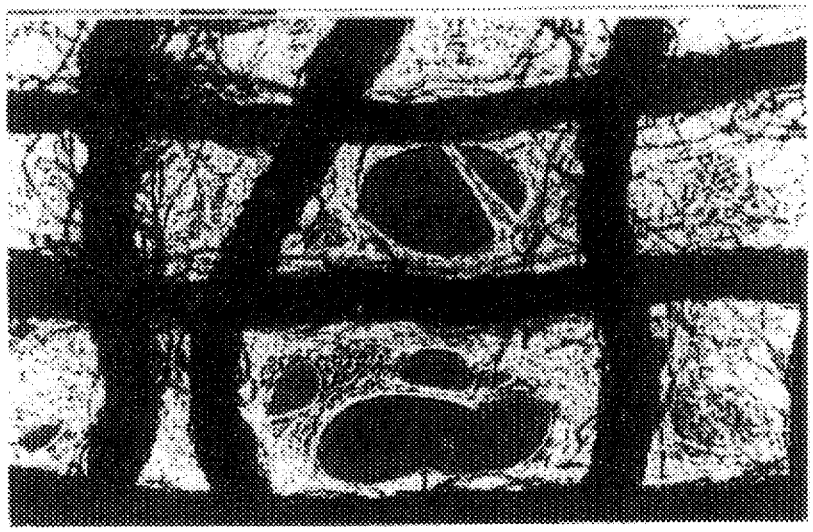
FIG. 4 shows a phase-contrast microphotograph and showing the 10th-day state of cells cultured by the method according to the present invention. 6.5 mm on the photograph is equivalent to 200 μm in an actual state.

In the Petri dish which has been prepared as noted above, human dermal fibroblasts suspended in 2 ml of cell culturing medium* were seeded at a final density of $3.3\times10^5$ cells/Petri dish, and cultured at 37° C. in a humidified atmosphere of 5% $CO_2$ and 95% air. On the first day of culture, the culture medium was replaced by a cell culture medium containing 0.1 mM L-ascorbic acid phospate magnesium salt (made by WAKO Pure Chemical Industries Ltd.). Thereafter, every two days, the culture medium was changed by a fresh one of the same composition, allowing the cells to be proliferated in a multilayer state on the gauze mesh (see FIG. 3 Photograph: phase-contrast microphotograph on the 8th day of culture). On the tenth day, it was found that the cells had been proliferated in a multilayer on the gauze mesh when the specimen was taken out together with the pipette physically by the silicon fixing part being broken with a surgical knife (FIG. 4 Photograph: phase-contrast microphotograph on specimen taken out on the 10th day of culture). The tubular part of the pipette was fixed vertically on the acryl plate supporting stand as given in Example 1 so as to hold the multilayer cells on the gauze mesh in gaseous phase and keep the lower end of the gauze immersed in the cell culture medium inside the Petri dish.

With the culture medium filled in the tubular part of the pipette, a culture medium was fed at a flow rate of about 1.0 ml/hr., maintaining the cells proliferated three-dimensionally.

Comparative Example 1

Figure 5:
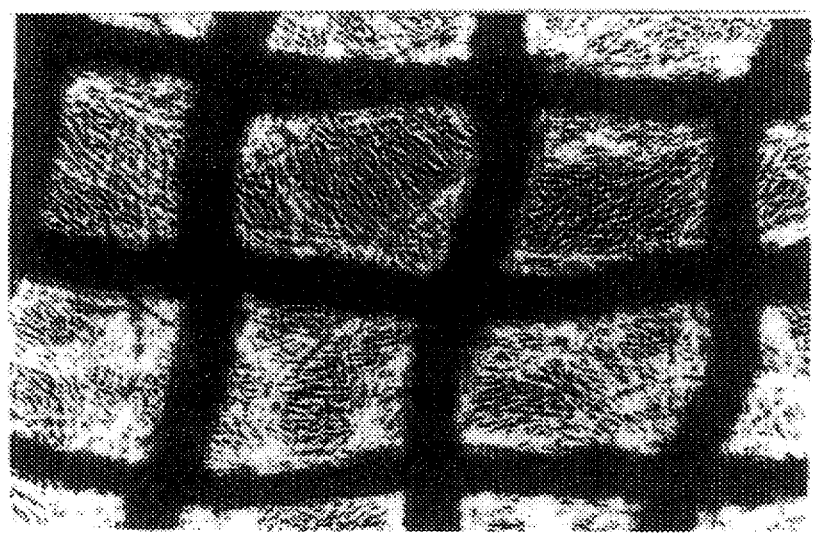
FIG. 5 shows a phase-contrast microphotograph and showing the 8th-day state of cells cultured as a comparative example in the present invention. 6.5 mm on the photograph is equivalent to 200 μm in an actual state.
Figure 6:
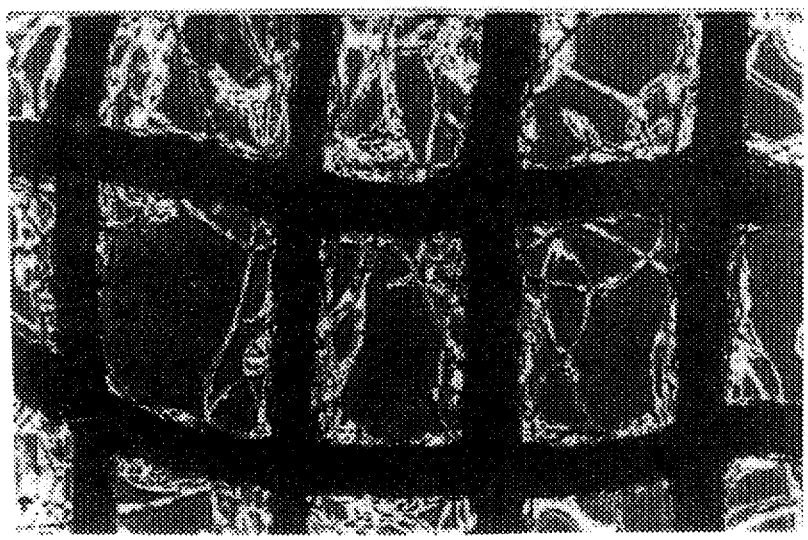
FIG. 6 shows a phase-contrast microphotograph and showing the 10th-day state of cells as a comparative example in the present invention. 6.5 mm on the photograph is equivalent to 200 μm in an actual state.

In Example 2, even in the case where the culture medium* was replaced every two days after the 1st day of culture, using a usual type of cell culture medium* containing no L-ascorbic acid phosphate magnesium salt, the cells were not proliferated in a multilayer state on a gauze mesh but merely formed a monolayer confluent on the gauze mesh (FIG. 5 Photograph: phase-contrast microphotograph on the 8th day of culture). On the 10th day of culture, the pipette was taken out physically from the body by the silicon fixing part being broken with a surgical knife, almost none of the cells were found adhered on the gauze mesh (FIG. 6 photograph: phase-contrast microphotograph after the specimen taken out on the 10th day of culture). The result clearly shows that the addition of ascorbic acid will cause the proliferation of the cells in a multilayer (three-dimensional) form on the medium-penetrating cell culture carrier.

Example 3

(A method for culturing animal cells three-dimensionally in a collagen gel containing a medium-penetrating gauze)

Figure 7:
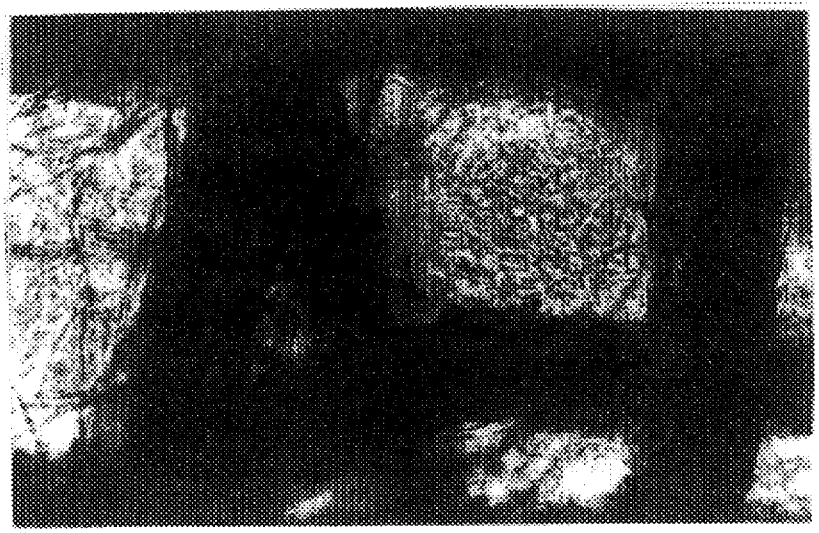
FIG. 7 shows a phase-contrast microphotograph and showing the 10th-day culture state of cells as an embodiment of the present invention. 16 mm on the photograph is equivalent to 200 μm in an actual state.

A pipette having its clasping end cut off into which the gauze having a suture and prepared in Example 1 was inserted and fixed at the tubular part on an acryl plate supporting stand. The portion of th gauze dampened by feeding a cell culture medium thereto in advance was immersed into a Petri dish in which, suspended in a cell culture medium* containing 2 ml of 0.24% type-I collagen, human dermal fibroblast were seeded in that Petri dish at a final density of $3.3\times10^5$ cells/Petri dish (φ35 mm: Falcon #1008). It was cultured at 37° C. in a humidified atmosphere of 5% $CO_2$ and 95% air, and embedded in a collagen gel together with cells. After three hours of culture, the collagen became completely gelatinized and semi-transparent. A pair of forceps were used to separate the Petri dish from the gel, and 2 ml of cell culture medium* was added, causing the gauze-containing gel to float in the Petri dish for continued culture. On the 1st day of culture and thereafter, in order that the gauze-containing gel was held in gaseous phase and the bottom end of the gauze was immersed in the cell culture medium* in the Petri dish, the tubular part of the pipette was vertically fixed on the acryl plate supporting stand. Under this condition, the culture medium was filled into the tube of the pipette and fed to the gel at a flow rate of 1.0 ml/hr., maintaining cells in a three-dimensional state in the gauze-containing gel. Incidentally, the surrounding gel containing no gauze gradually contrasted, while the gel portion containing the medium-penetrating gauze was hindered from physical contraction. Even on the 10th day of culture, the cells in the gel containing the medium-penetrating gauze spread well therein. Favorable cell morphology could be observed with a phase contrast microscope (FIG. 7: Photograph: phase-contrast microphotograph on the 10th day of culture).

Comparative Example 2

Figure 8:
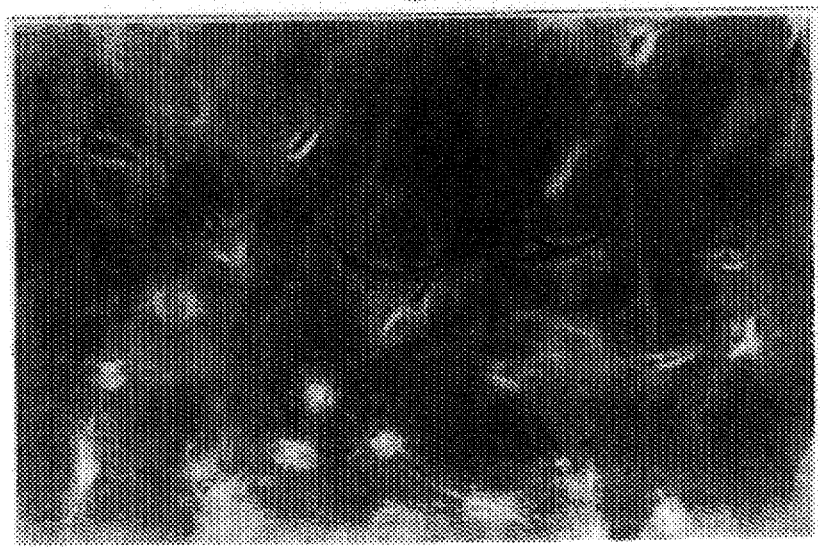
FIG. 8 shows a phase-contrast microphotograph and showing the 6-hr. state of gels as a comparative example of the present invention. 32 mm on the photograph is equivalent to 200 μm in an actual state.
Figure 9:
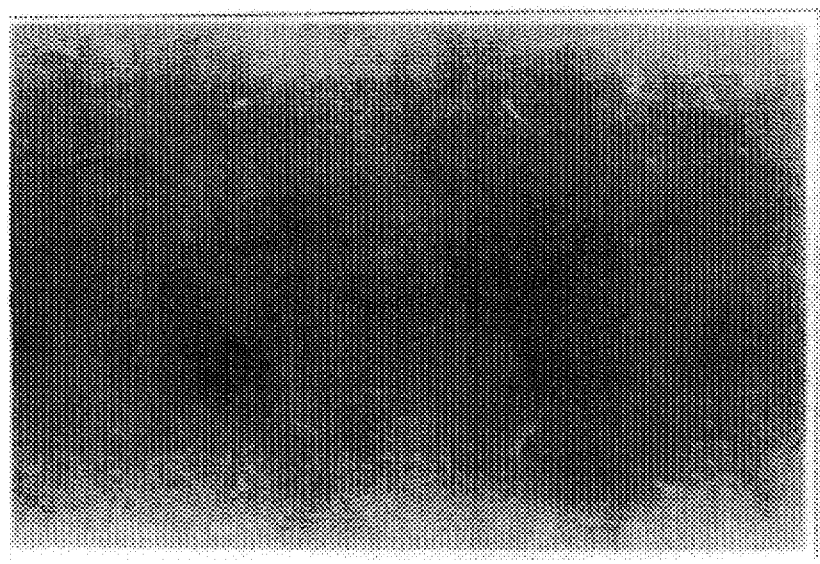
FIG. 9 shows a phase-contrast microphotograph and showing the 4th-day state of gels as a comparative example of the present invention. 32 mm on the photograph is equivalent to 200 µm in an actual state.

In a Petri dish, human dermal fibroblasts suspended in a cell culture medium* containing 0.24% type-I collagen were seeded at a final density of $3.3\times10^5$ cells/Petri dish (φ35 mm: Falcon #1008). It was cultured at 37° C. in a humidified atmosphere of 5% $CO_2$ and 96% air, allowing the cells embedded in collagen gel. After 3 hours of culture, the collagen became completely gelatinized and semi-transparent. A pair of forceps were used to separate the Petri dish from the gel, and 2 ml of cell culture medium* was added, causing the gauze-containing gel to float in the Petri dish for continued culture. Thereafter, every two days, the cell culture medium was changed to allow the culture to continue. The gel slowly contracted. On the 10th day of culture, it became disk-shaped with a mean diameter of approximately 7 mm. After six hours of culture the cells in the gel had spread well, showing favorable cell morphology (FIG. 8: Phase contrast microphotograph in the sixth hour of culture), but on the 4th day of culture, due to the contraction of the gel, no favorable cell morphology could be observed with a phase-contrast microscope (FIG. 9: Phase contrast microphotograph on the 4th day of culture).

Example 4

(Culture using a single piece of gauze)

Figure 10:
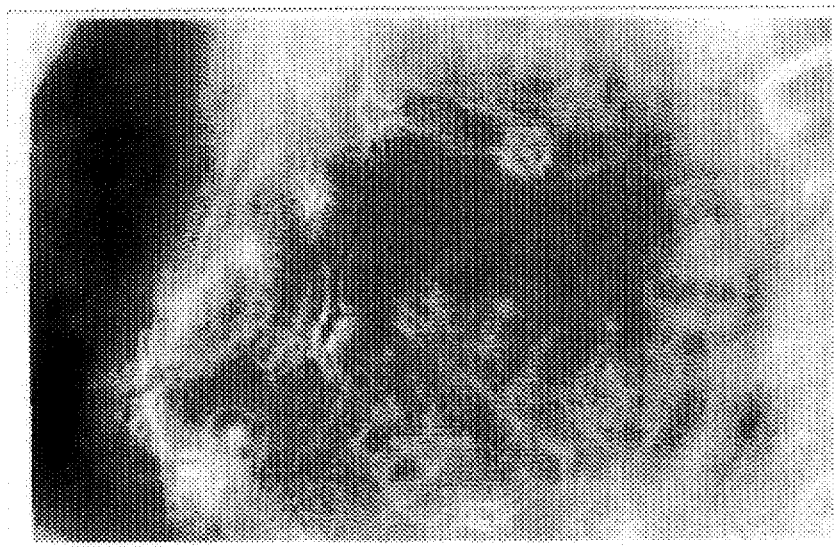
FIG. 10 shows a phase-contrast microphotograph and showing the 6th-hr. state of gauze-gels as a comparative example of the present invention. 32 mm on the photograph is equivalent to 200 µm in an actual state.
Figure 11:
FIG. 11 shows a phase-contrast microphotograph and showing the 10th-day state of gauze-gels as a comparative example of the present invention. 16 mm on the photograph is equivalent to 200 µm in an actual state.

A piece of gauze having a size of about 2×2 cm was dampened with a cell culture medium* beforehand. It was then immersed into a Petri dish in which human dermal fibroblasts suspended in 2 ml of cell culture medium* containing 0.24% type-I collagen were seeded at a final density of $3.3\times10^5$ cells/Petri dish (φ35 mm: Falcon #1008). It was cultured at 37° C. in a humidified atmosphere of 5% $CO_2$ and 95% air, and was embedded in collagen gel, together with the cells. After three hours of culture, the collagen became completely gelatinized and semi-transparent. A pair of forceps were used to separate the Petri dish from the gel, and 2 ml of cell culture medium* was added, causing the gauze-containing gel to float in the Petri dish for continued culture. Thereafter, every two days, cell culture medium* changed to allow the culture to continue. The surrounding gel containing no gauze slowly contracted, while the gel portion containing the gauze was physically inhibited from the contraction. On the 10th day of culture, it became disk-shaped with a mean diameter of approximately 25 mm. The cells in the gel containing the gauze had spread well in the 6th hour of culture, showing a good cell morphology (FIG. 10 Photograph: Phase-contrast microphotograph in the 6th hour of culture). Even on the tenth day of culture, it was found that the cells in the gel containing the medium-penetrating gauze spread therein and a good cell structure could be observed with a phase-contrast microscope (FIG. 11 Photograph: phase-contrast microphotograph on the 10th day of culture).

Example 5

(Three-dimensional culture device)

Figure 12:
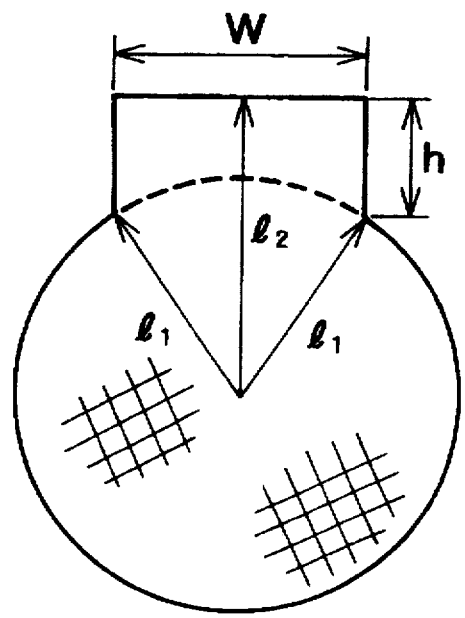
FIG. 12 shows a plan view showing another gauze carrier as an embodiment of the present invention.
Figure 13:
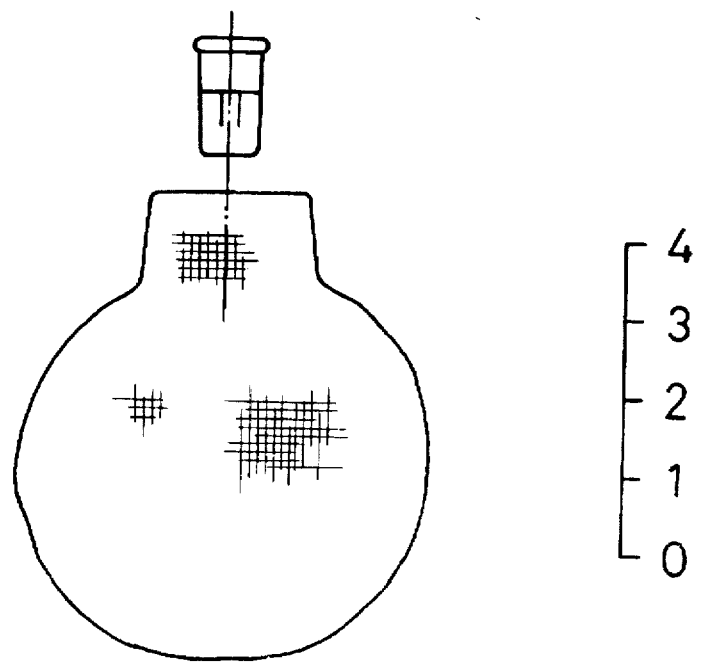
FIG. 13 shows a plan view showing the state corresponding to FIG. 12.
Figure 14:
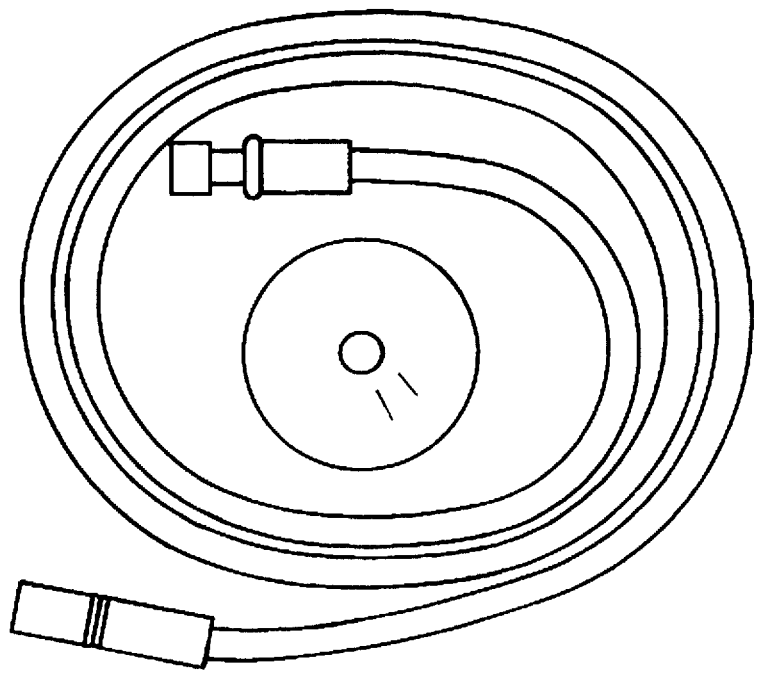
FIG. 14 shows a perspective diagram showing a sterilized extension tube.
Figure 15:
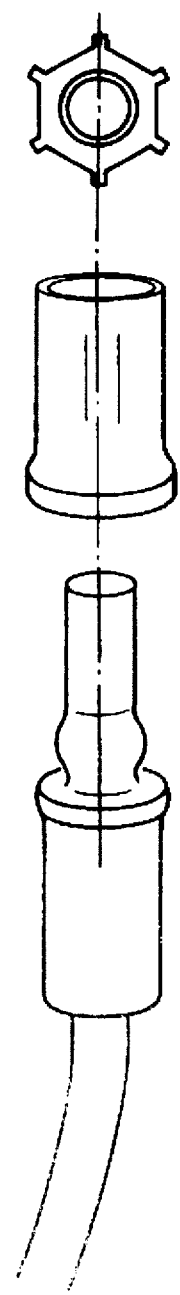
FIG. 15 shows a perspective diagram showing the state in which the tip of the tube in FIG. 14 is cut.
Figure 16:
FIG. 16 shows a perspective diagram showing the tip of the tube on which gauze is fixed.
Figure 17:
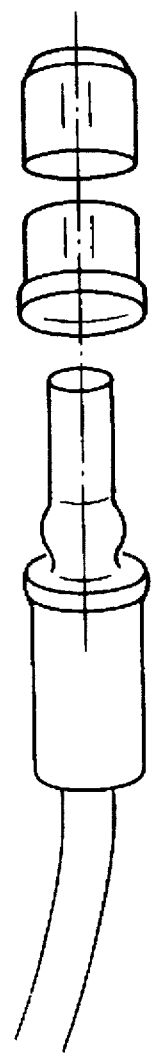
FIG. 17 shows a perspective diagram showing the state in which the sack for the tip of the tube is cut.
Figure 18:
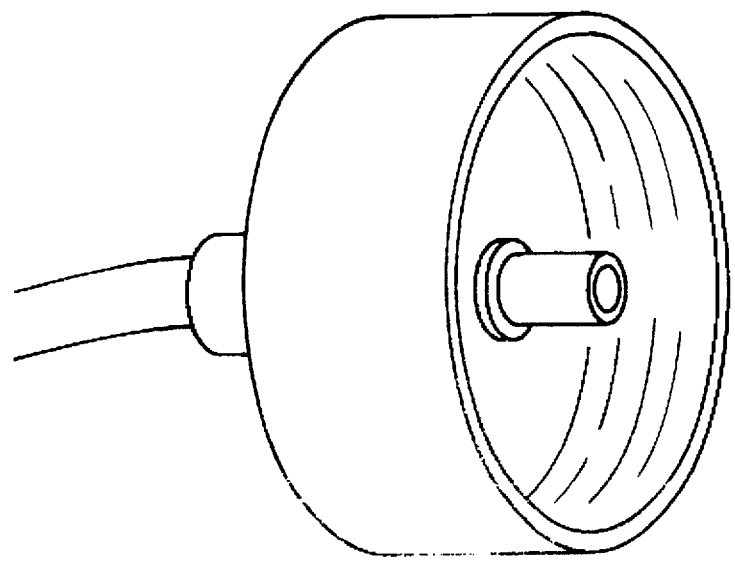
FIG. 18 shows a perspective diagram showing the state in which an extension tube whose tip sack has been cut is inserted into the cap of a conical tube.
Figure 19:
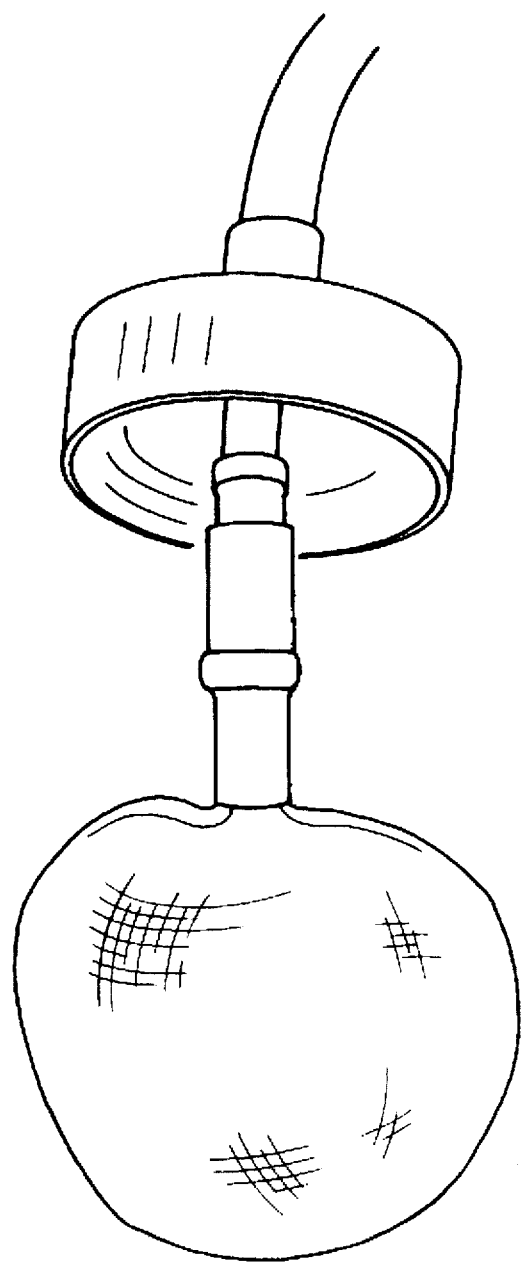
FIG. 19 shows a perspective diagram showing the state in which the tube on which gauze is fixed as in FIG. 19 is inserted and fixed.
Figure 20:
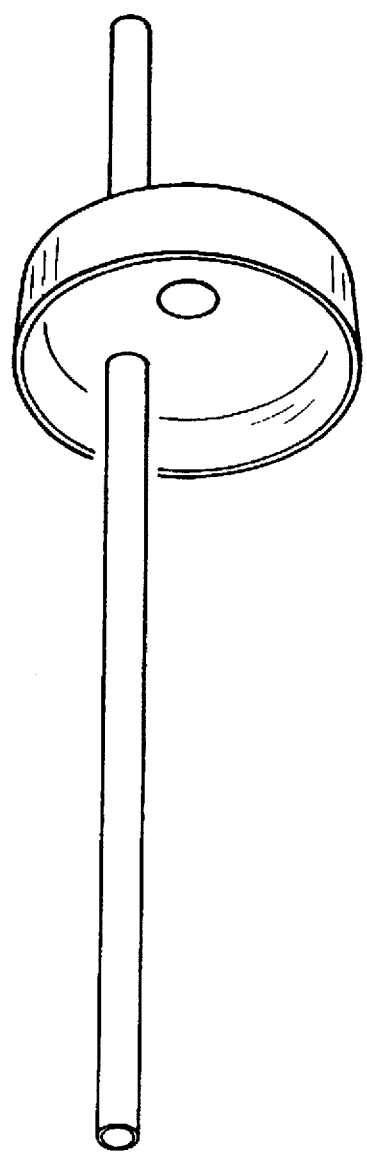
FIG. 20 shows a perspective diagram showing the state in which the body inserted and fixed in FIG. 19 is mounted on the conical cap body.

In addition, sterilized gauze type-III listed in Japanese Pharmacopoeia (K-pine; made by Kawamoto Bandaging Materials Co., Ltd.) was cut aseptically to a circular form, as shown in FIG. 12, with a diameter of 5.0 cm and having a projection designed for fixation (FIG. 13). The projection of the gauze cut as indicated above was inserted and fixed into a sterilized extension tube (Serfield SF-ET 5527, with a length of 7.5 cm and a content of 5.5 ml, made by Telmo Co., Ltd. FIG. 14). The sack of the tip thereof was aseptically cut (FIG. 15). With 3 to 10 mm left, the tube was then cut aseptically, preparing the tip of a gauze-fixing tube (FIG. 16). In the cap of a sterilized conical tube (Falcon #2070) with a volume of 50 ml, a circular hole with a diameter of approximately 7 mm was pierced, having the sterilized extension tube with the tip sack aseptically (FIG. 17) inserted and fixed into said hole (FIG. 18). Further onto that tip, the tube at the tip of said gauze-fixing tube was inserted and fixed (FIG. 19). Thereafter, the conical tube body was mounted (FIG. 20). This extension tube was mounted on a peristaltic pump (MP-3A, made by Tokyo Rika). The end having no gauze fixed thereon was placed into a bottle full of a cell culture medium which was fed to the end on which the gauze was fixed. Then, absorbed by the filaments comprising the gauze, the culture medium was distributed all over the gauze. As it became excessive slowly, the medium started to drop with the gauze as a medium-penetrating carrier until it filled the conical tube. The penetrating amount of the culture medium can be controlled from 10 μl to 3.3 ml/min. by any of the following:

<1> by adjusting the dial on the peristaltic pump;
<2> by using another extension tube with a different diameter; or,
<3> by replacing inner gears of the peristaltic pump.

Figure 21:
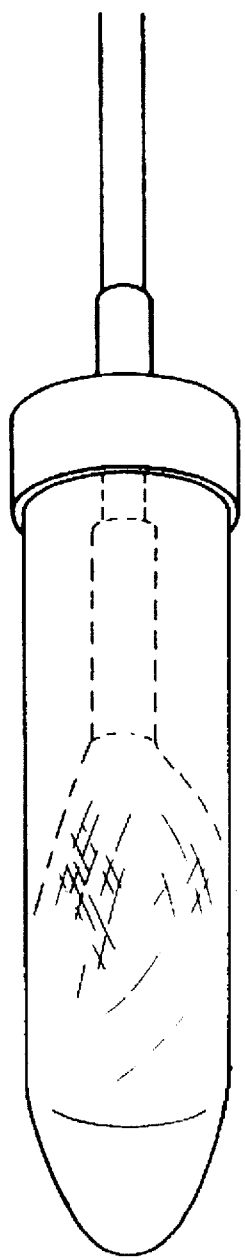
FIG. 21 shows a perspective diagram showing the state in which a plastic pipette is inserted and fixed on the cap of the conical tube.
Figure 22:
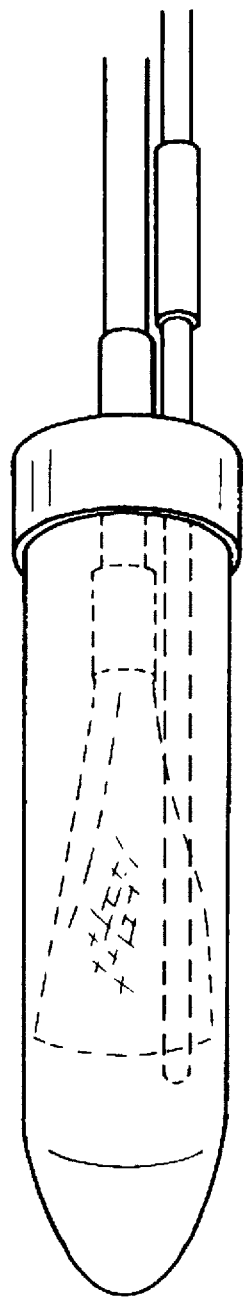
FIG. 22 shows a perspective diagram illustrating a circulating culture vessel.

Moreover, in said cap of the conical tube, a circular hole having a diameter of approximately 4 mm was pierced, a sterilized plastic pipette was cut to an appropriate length (Falcon #7520, 1 ml) and was inserted into that hole (FIG. 21). Thereafter, into this cap, a piece of gauze was mounted as described above, and the tube end having no gauze fixed thereon is mounted on the top end of the pipette. This makes it ready to circular a cell culture medium in a single conical tube (FIG. 22).

Example 6

(A method for culturing animal cells three-dimensionally)

A circular piece of gauze attached with an extension (a diameter of 5.0 cm) as produced in Example 5 was placed on the bottom surface of the hydrophobic polystyrene culture Petri dish (Falcon #1007, φ60 mm). Said circular gauze portion was coated with approximately 0.8 ml of 0.25% type-I collagen solution (CELLGEN I-PC; made by Koen Co., Ltd.) to be dried in the air aseptically; and, if required, the bottom surface of said dish attached with gauze was irradiated by ultraviolet ray (a short wave length of 254 mm) for about 30 minutes.

Figure 23:
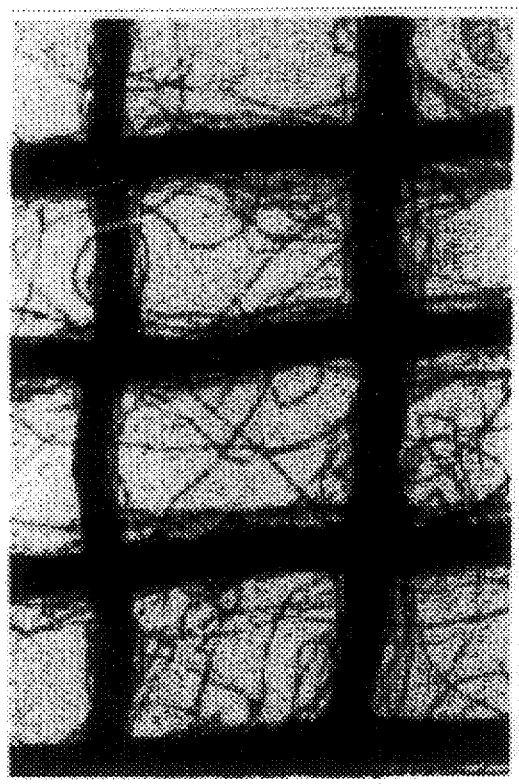
FIG. 23 shows a phase-contrast microphotograph and showing the state where cells are allowed to proliferate in a multilayer state up to the 10th day. 16 mm on the photograph is equivalent to 500 µm in an actual state.

In the foregoing Petri dish, human dermal fibroblasts suspended in 5.0 ml of cell culture medium* containing 0.1 mM L-ascorbic acid phosphate magnesium salt (made by Wako Pure Chemical Industries, Ltd.) were seeded at the final density of $8.0 \times 10^5$ cells/dish and cultured at 37° C. in a humidified atmosphere of 5% $CO_2$ and 95% air. During the process, the culture medium was changed to a fresh one every two days, allowing the cells to be proliferated in a multilayer state on the gauze mesh up to the 10th day of culture. (FIG. 23 Photograph phase-contrast microphotograph).

Figure 24:
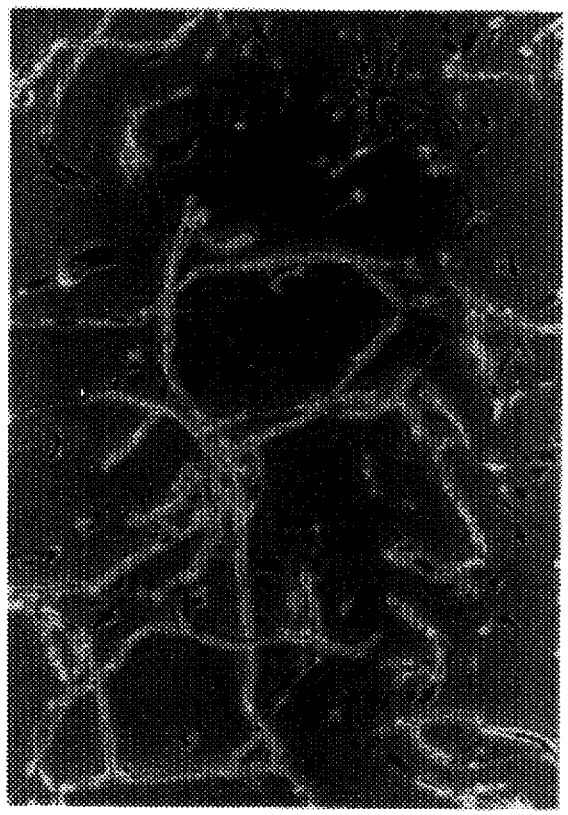
FIG. 24 shows a phase-contrast microphotograph and showing the state of a Petri dish after a gauze carrier is removed. 16 mm on the photograph is equivalent to 500 µm in an actual state.
Figure 25:
FIG. 25 shows a phase-contrast microphotograph and showing the state of the adhesion of cells to a gauze carrier after a gauze carrier is removed. 16 mm on the photograph is equivalent to 500 µm in an actual state.

On the 10th day of culture, a projection part of the gauze was picked up by a pair of forceps physically allowing the cells proliferated in a multilayer form on the gauze mesh to be detached from the dish. It was found that essentially none of the cells remained on the dish from which said gauze was detached (FIG. 24: Photograph: phase-contrast microphotograph). Rather, most of the cells were adhered on the gauze which was removed from the dish (FIG. 25: Photograph: phase-contrast microphotograph).

Figure 26:
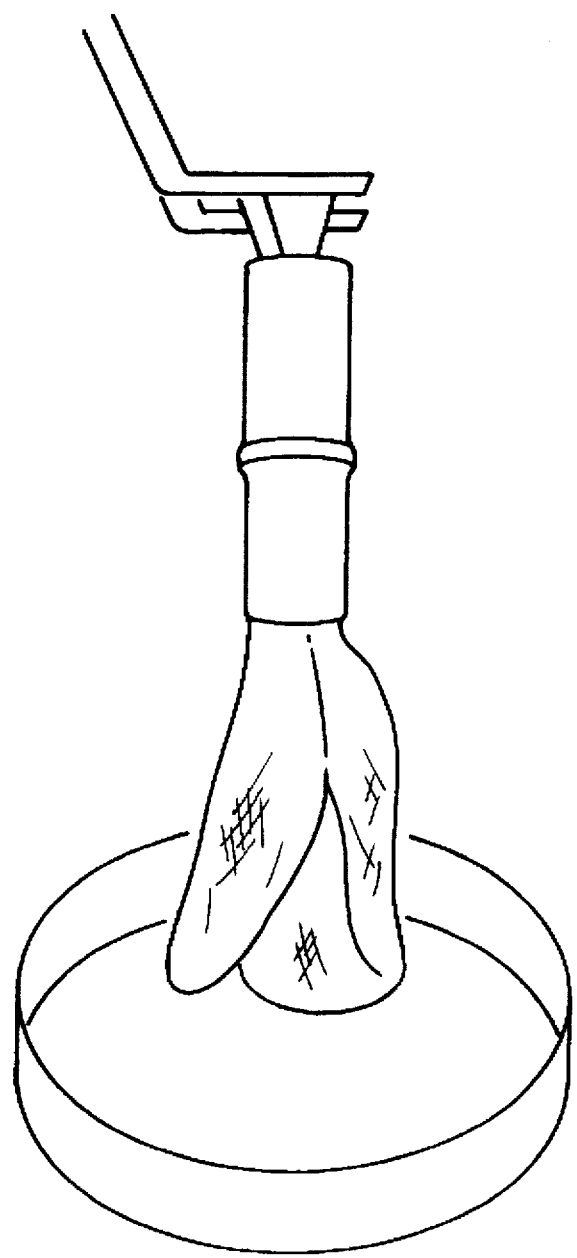
FIG. 26 shows a perspective diagram showing a carrier for circulating culture.
Figure 27:
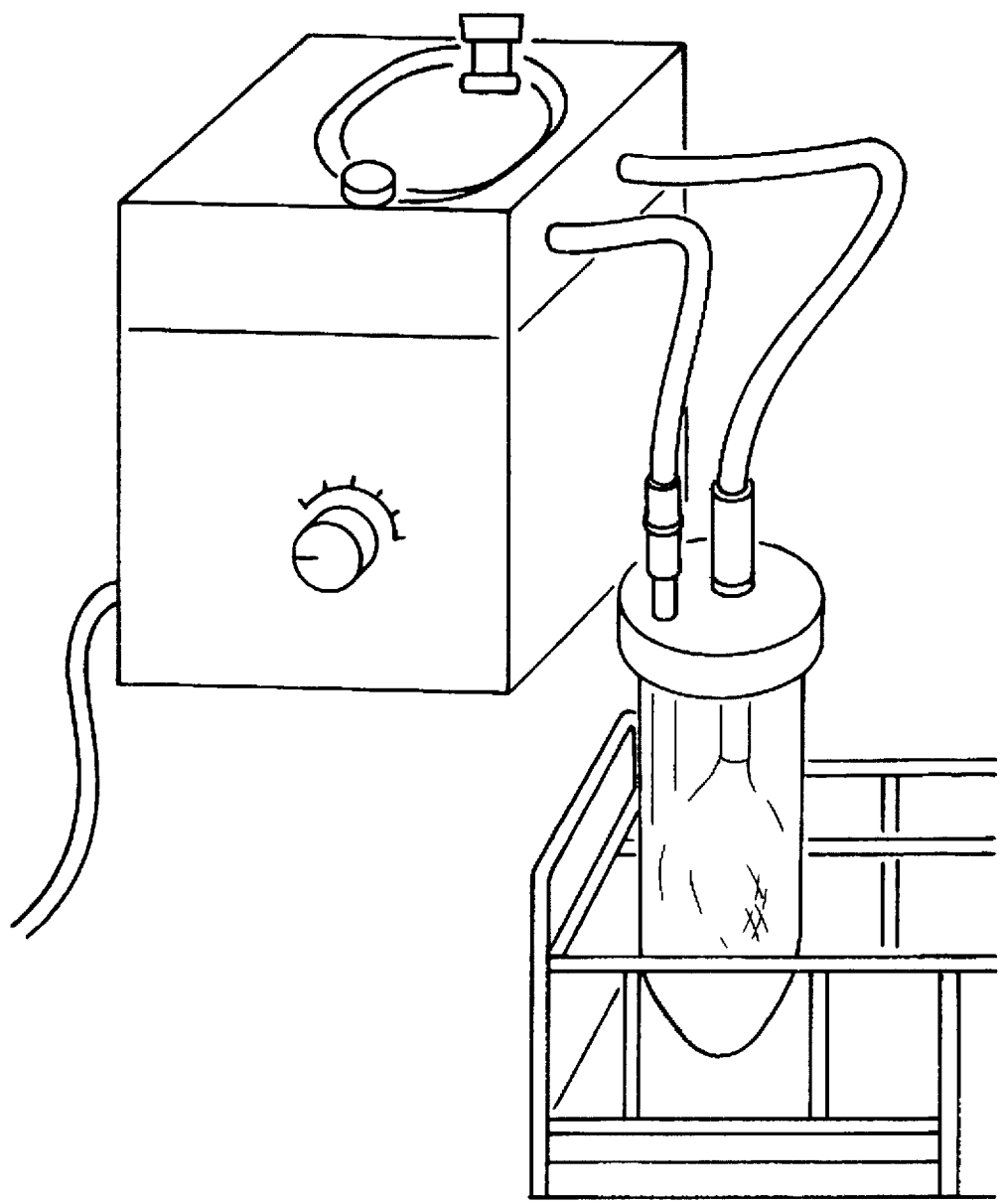
FIG. 27 shows a perspective diagram showing the state of circulating culture.
Figure 28:
FIG. 28 shows a phase-contrast microphotograph and showing the state where multi cellular aggregate is formed. 16 mm on the photograph is equivalent to 500 µm in an actual state.

The gauze specimen prepared so as to have a multilayer of proliferated cells attached was allowed to adhere on the medium-penetrating device, including the one produced in Example 5. While 10 ml of similar culture medium was circulated at a flow rate of about 0.8 ml/min., it was cultured in at 37° C. in a humidified atmosphere of 5% $CO_2$ and 95% air (FIGS. 26 and 27). Every two days, the culture medium was changed to a fresh one, and then the gauze portion was taken out after 3 weeks of culture while a culture medium was allowed to penetrate. When it was observed by means of a phase contrast microscope, the result showed that each of those cells exhibited self-assembly capability around the thin fabrics of gauze, forming multicellular aggregate in which the gauze fiber was distributed all over the body (FIG. 28: Photograph phase-contrast microphotograph). Subsequently, the above multicellular aggregate was fixed with formalin and dehydrated. Thereafter, the aggregate was embedded into resin for optical microscopic observation, sliced in 4 μm thickness and provided with double color dyeing with Comdssi blue and hematoxylin, letting the specimen exposed to internal histological structure observation.

Figure 29:
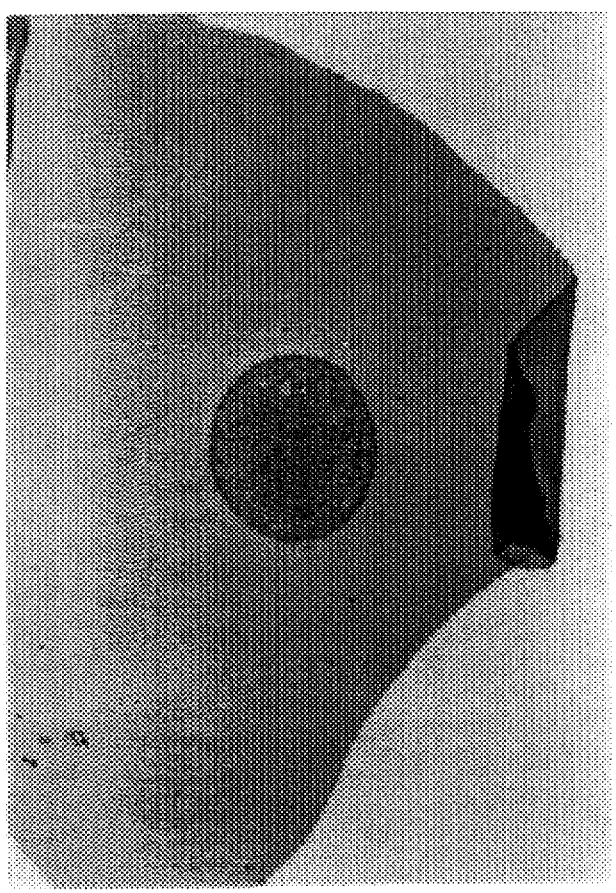
FIG. 29 shows a photograph showing spheroid for comparison. 19 mm on the photograph is equivalent to 500 µm in an actual state.
Figure 30:
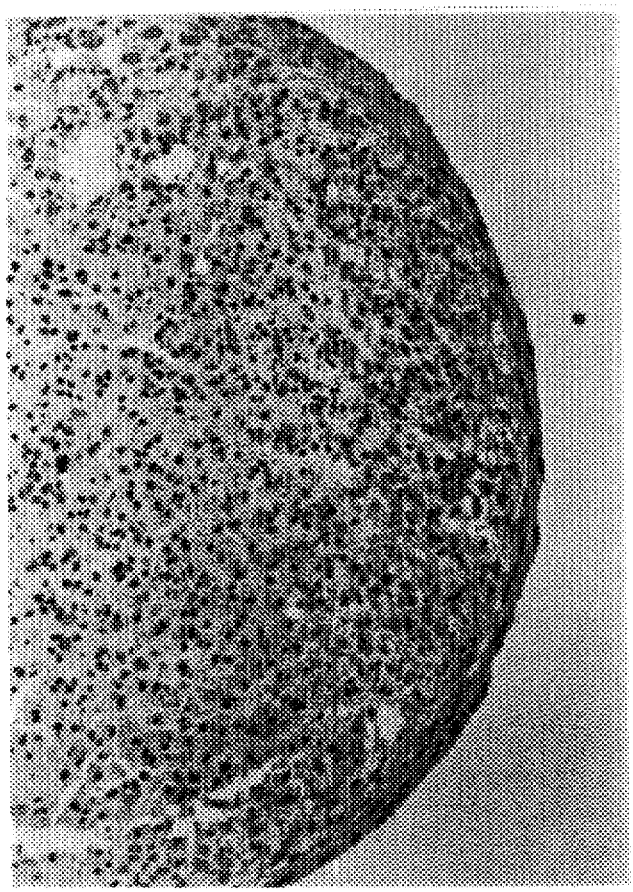
FIG. 30 shows an enlarged diagram of FIG. 29. 19 mm on the photograph is equivalent to 100 µm in an actual state.
Figure 31:
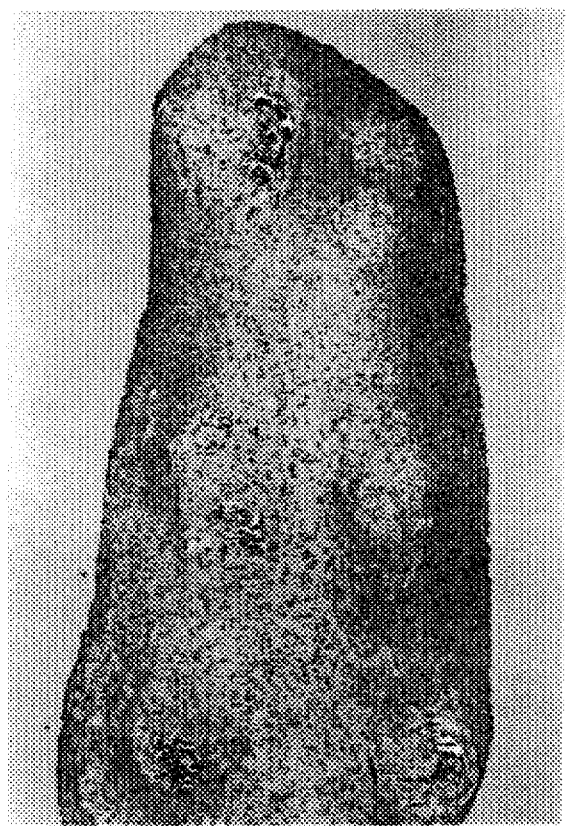
FIG. 31 shows a photograph showing spheroid in this invention. 19 mm on the photograph is equivalent to 500 µm in an actual state.
Figure 32:
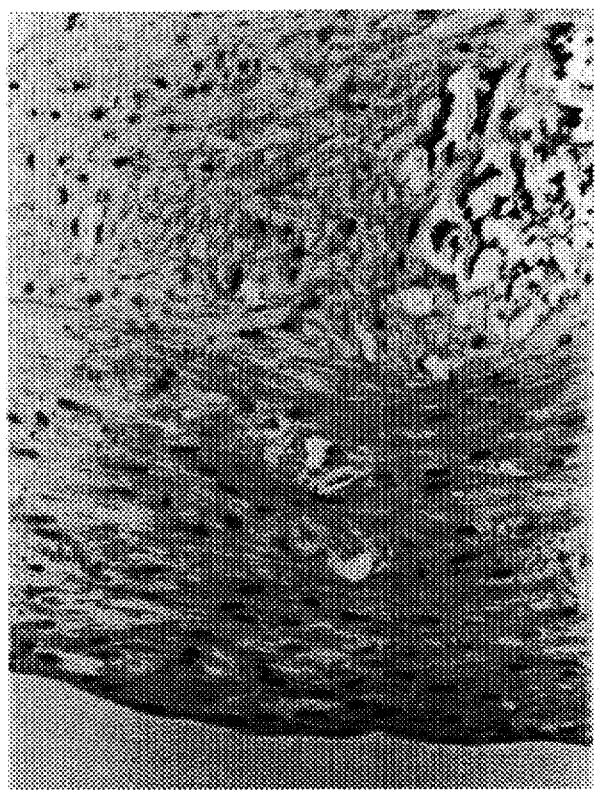
FIG. 32 shows an enlarged diagram of FIG. 31. 19 mm on the photograph is equivalent to 100 µm in an actual state.

Comparison was made between the specimen in this example and the spheroid having a diameter of about 600 μm and cultured for three weeks after being produced by the conventional processes using the same human dermal fibroblasts. The results revealed that in spite of the fact that there were seen quite a few piknotic or cell debris inside the spheroid (FIGS. 29 and 30). There were mostly none of the piknotic cells observed on the section of multicellular aggregate contained in the piece of gauze having a longer diameter of more than 5 mm and a shorter diameter of approximately 2 mm. Between the cells Comdssi blue positive fiber biosynthesis were noticed (FIGS. 31 and 32), and it was presumed that the internal structure composing cells had an extremely favorable living cell activity.

Comparative Example 3

Figure 33:
FIG. 33 shows a phase-contrast microphotograph and showing the state of gauze on the 10th day as a comparative example. 16 mm on the photograph is equivalent to 500 µm in an actual state.

In Example 6, another attempt was made. The cells were suspended in a usual cell culture medium* including no L-ascorbic acid phosphate magnesium salt, and seeded of the same final density, then the culture medium was changed every two days and cell culture was continued for 10 days. On the 10th day of culture, it was observed that the cells were not proliferated in a multilayer form on the gauze mesh; rather, monolayer confluent was formed on the gauze mesh (FIG. 33: Photograph: phase-contrast microphotograph).

Figure 34:
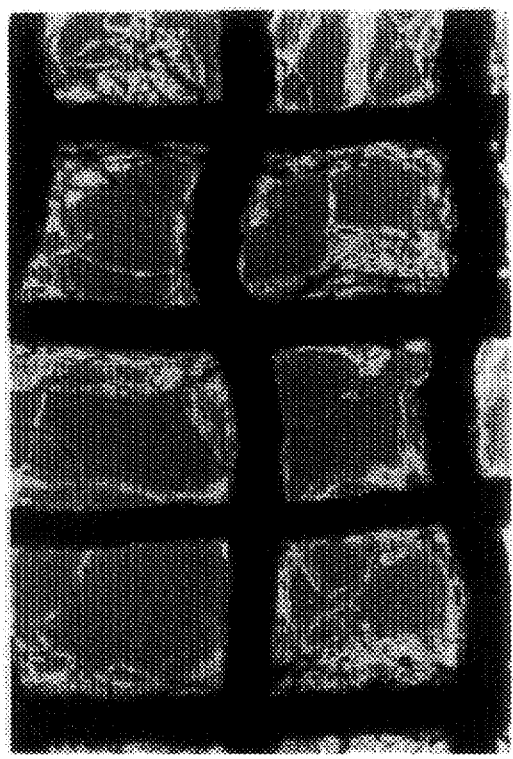
FIG. 34 shows a phase-contrast microphotograph and showing the state of gauze after the gauze is removed from a Petri dish. 16 mm on the photograph is equivalent to 500 µm in an actual state.
Figure 35:
FIG. 35 shows a phase-contrast microphotograph and showing the state of a Petri dish after the gauze is removed therefrom. 16 mm on the photograph is equivalent to 500 µm in an actual state.

In the same way as shown in Example 6, the gauze projection part was picked up by a pair of forceps, allowing the gauze mesh to be removed from the Petri dish (FIG. 34: Photograph: phase-contrast microphotograph). It was then found that almost none of the cells were attached on the removed gauze (FIG. 35: Photograph: phase-contrast microphotograph). The results of the foregoing attempt showed clearly the fact that addition of ascorbic acid made the cells proliferated in a multilayer (three-dimensional) form on the medium-penetrating cell culture carrier.

As described above in detail, the instant invention makes it possible to culture animal cells three-dimensionally so that they self-assemble their own tissue in the same way as they are in the tissue or organ from which they are derived.

A mesh body disclosed as a carrier according to the present invention, in particular, not only provides medium-penetrating properties, but also makes the cells to be cultured more tensioned, permitting a three-dimensional, highly efficient culture of cells so as to simulate the state of cells in a living organism more closely.

Furthermore, the carrier device according to the present invention is exceedingly easy to handle. As compared with the three-dimensional aggregate given by the conventional culture method, including the spheroid culture method, the aggregate obtained by the culture method according to the present invention can be more freely controlled in respect of size and the number of constituent cells. This is useful in that a sufficient number of cells can be secured for the assay of the cell activity.

We claim:

1. A cell culture device, comprising:
   a medium-penetrating cell culture carrier comprising a plurality of natural or synthetic threads or a woven body thereof, and
   a means for feeding a culture medium to said medium-penetrating cell culture carrier,
   wherein said medium-penetrating cell culture carrier is physically connected to said means for feeding the culture medium, and
   wherein (1) said means for feeding the culture medium is a pipette, or (2) said means for feeding the culture medium is physically connected to said medium-penetrating cell culture carrier by a natural or synthetic thread of said carrier or by a suture, or (3) said means for feeding the culture medium is physically connected to said medium penetrating cell culture carrier by a tube.

2. The cell culture device according to claim 1, wherein said medium-penetrating cell culture carrier is a mesh body.

3. The cell culture device according to claim 1, wherein said medium-penetrating cell culture carrier is biodegradable in a living organism.

4. The cell culture device according to claim 1, wherein said medium-penetrating cell culture carrier is coated with a surface material to adhere cells thereon.

5. The cell culture device according to claim 4, wherein said surface material adheres cells selectively and locally to said carrier.

6. The cell culture device according to claim 4, wherein said surface material is an extracellular matrix component, gelatin, lectin, Mytilidae-derived adhesive protein, polylysine, adhesive oligopeptide or thrombospongin.

7. The cell culture device according to claim 6, wherein said extracellular matrix component is collagen, fibronectin, hydronectin, laminin, proteoglycan, or glycosaminoglycan.

8. The cell culture device according to claim 1, wherein said medium-penetrating cell culture carrier is embedded inside a gel containing an extracellular matrix component.

9. The cell culture device according to claim 1, wherein said means for feeding the culture medium includes a reservoir bottle for holding the culture medium.

10. The cell culture device according to claim 1, wherein said means for feeding the culture medium includes a peristaltic pump.

11. The cell culture device according to claim 1, wherein said means for feeding the culture medium includes a means for controlling the amount of culture medium which penetrates into said medium-penetrating cell culture carrier.

12. The cell culture device according to claim 1, which includes a means for circulating the culture medium.

13. A cell culture device, comprising:
    a container having a surface which defines an interior of said container,
    a tube having a first end and a second end, said tube passing through said container surface such that said first end of said tube is disposed within said interior of said container and said second end of said tube is disposed outside of said container, and
    a woven body comprised of a plurality of natural or synthetic threads which is physically connected to said first and of said tube.

14. The cell culture device according to claim 13, wherein said container is a glass tube having a cap.

15. The cell culture device according to claim 14, wherein said tube passes through said cap.

16. A method for culturing cells using the cell culture device according to claim 1, which comprises:
    contacting said medium-penetrating cell culture carrier with a solution containing cells to be cultured,
    feeding medium to the medium-penetrating cell culture carrier using said means for feeding the culture medium, and
    culturing the cells under conditions suitable for growth.

17. The method according to claim 16, wherein the culture medium includes ascorbic acid or a salt thereof.

* * * * *